(12) United States Patent
Misaki et al.

(10) Patent No.: US 11,396,524 B2
(45) Date of Patent: Jul. 26, 2022

(54) HYDRATE CRYSTAL OF 3',3'-CGAMP

(71) Applicant: Yamasa Corporation, Choshi (JP)

(72) Inventors: Takamatsu Misaki, Choshi (JP); Yoshida Ko, Choshi (JP); Ishige Kazuya, Choshi (JP)

(73) Assignee: Yamasa Corporation, Choshi (JP)

( * ) Notice: Subject to any disclaimer, the term of this patent is extended or adjusted under 35 U.S.C. 154(b) by 0 days.

(21) Appl. No.: 17/256,078

(22) PCT Filed: Jun. 25, 2019

(86) PCT No.: PCT/JP2019/025052
§ 371 (c)(1),
(2) Date: Dec. 24, 2020

(87) PCT Pub. No.: WO2020/004358
PCT Pub. Date: Jan. 2, 2020

(65) Prior Publication Data
US 2021/0269471 A1    Sep. 2, 2021

(30) Foreign Application Priority Data

Jun. 27, 2018  (JP) .............................. JP2018-122255

(51) Int. Cl.
C07H 21/02    (2006.01)
C07H 1/06    (2006.01)

(52) U.S. Cl.
CPC ............... *C07H 21/02* (2013.01); *C07H 1/06* (2013.01); *C07B 2200/13* (2013.01)

(58) Field of Classification Search
CPC .................................... C07H 21/02; C07H 1/06
See application file for complete search history.

(56) References Cited

U.S. PATENT DOCUMENTS 11,058,758 B2 *  7/2021  Ishii .................... A61P 35/00
2017/0319680 A1   11/2017 Ishii et al.

FOREIGN PATENT DOCUMENTS

CN    106190999 A    12/2016
WO    WO-2016/079899 A1    5/2016

OTHER PUBLICATIONS

Davies et al., "Coordinated regulation of accessory genetic elements produces cyclic di-nucleotides for V. cholerae virulence," Cell 149(2):358-370 (2012) (26 pages).
Gao et al., "Cyclic [G(2',5')pA(3',5')p] is the metazoan second messenger produced by DNA-activated cyclic GMP-AMP synthase," Cell 153(5):1094-1107 (2013) (25 pages).
Gao et al., Identification and characterization of phosphodiesterases that specifically degrade 3'3'-cyclic GMP-AMP, Cell Res. 25(5):539-550 (2015).
Hallberg et al., "Hybrid promiscuous (Hypr) GGDEF enzymes produce cyclic AMP-GMP (3', 3'-cGAMP)," Proc. Natl. Acad. Sci. U.S.A. 113(7):1790-1795 (2016).
Hyodo et al., "Synthesis of cyclic bis(3'-5')diguanylic acid (c-di-GMP) analogs," Tetrahedron 62:3089-3094 (2006).
International Search Report dated Sep. 17, 2020 for PCT International Application No. PCT/JP2019/025052, Misaki et al., "Hydrate Crystal of 3', 3'-CGAMP," filed Jun. 25, 2019 (5 pages).
Kellenberger et al., "RNA-based fluorescent biosensors for live cell imaging of second messengers cyclic di-GMP and cyclic AMP-GMP," J. Am. Chem. Soc. 135(13):4906-4909 (2013) (8 pages).
Tokyo Chemical Industry Co., Ltd., "Nucleosides, nucleotides, nucleic acids and related reagents," 2016 (14 pages).
Wang et al., "Synthesis of all possible canonical (3'-5'-linked) cyclic dinucleotides and evaluation of riboswitch interactions and immune-stimulatory effects," J. Am. Chem. Soc. 139(45):16154-16160 (2017).
Caira, "Crystalline Polymorphism of Organic Compounds," Top. Curr. Chem. 198:163-208 (1998).
Extended European Search Report for European Patent Application No. 19824797.5, dated Jul. 30, 2021 (9 pages).
Wang et al., Supplement to "Synthesis of All Possible Canonical (3'-5'-Linked) Cyclic Dinucleotides and Evaluation of Riboswitch Interactions and Immune-Stimulatory Effects," J. Am. Chem. Soc. 139(45):16154-16160 (2017) pp. S1-S58 and cover sheet (59 pages total).
"Nucleosides, nucleotides, nucleic acids, and related reagents," Tokyo Chemical Industries L3014:1-14 (2016).
Notice of Reasons for Refusal dated Feb. 8, 2022, for Japanese Patent Application No. 2020-527529, Misaki et al., "Hydrate crystals of 3', 3'-cGAMP," filed Jun. 25, 2019 (6 pages).

\* cited by examiner

*Primary Examiner* — Layla D Berry
(74) *Attorney, Agent, or Firm* — Clark & Elbing LLP; Susan M. Michaud

(57) ABSTRACT

Among commonly known 3',3'-cGAMP is a lyophilized product. The lyophilized product needs a lyophilizer during the manufacture. This, itself, causes a limitation in scale-up for mass production. Thus, it has been desired to develop and obtain a large amount of their crystals in a simple manner without using a special apparatus such as a lyophilizer. In addition, conventionally known lyophilized products or ethanol precipitates are highly hygroscopic. Hence, the present invention addresses the problem of providing an easy-to-handle crystal with excellent shelf life. A hydrate crystal of 3',3'-cGAMP according to the invention may be either a crystal of alkali metal salt or a crystal of free acid. Either is less hygroscopic than existing powder. Thus, each is easy to handle in various purposes and is thus useful as a pharmaceutical raw material or the like.

9 Claims, 6 Drawing Sheets

[Fig. 1]
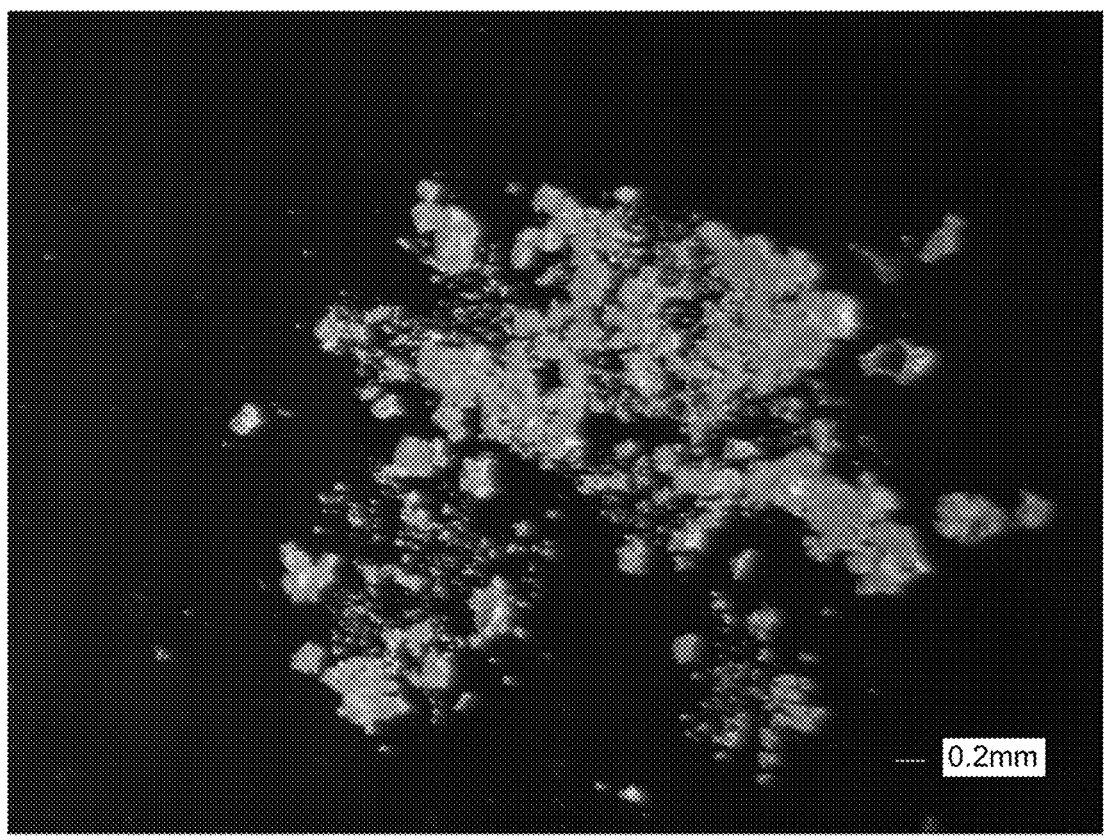
[Fig. 2]
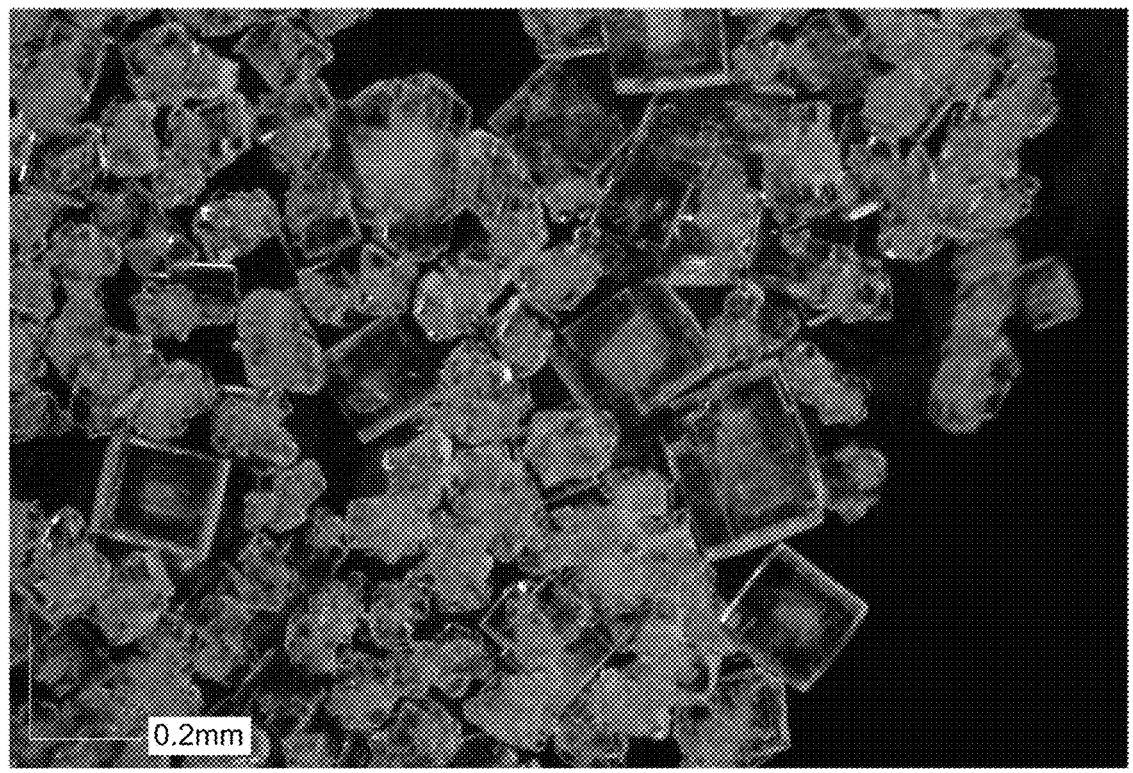

[Fig. 3]
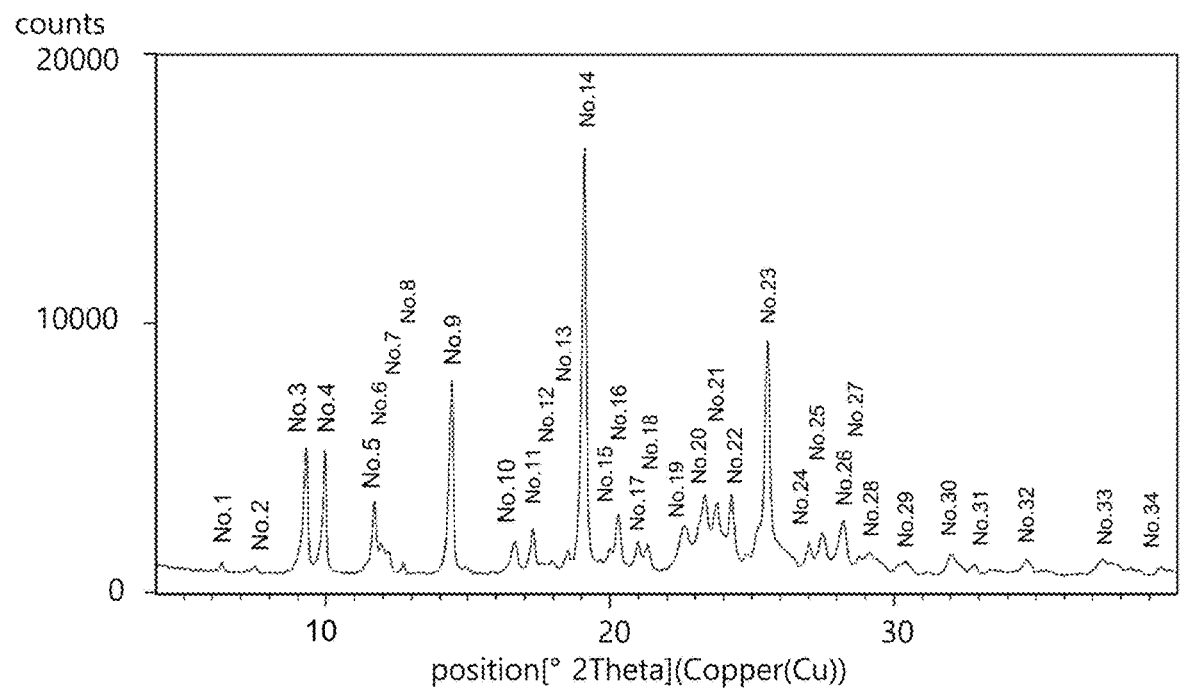
[Fig. 4]
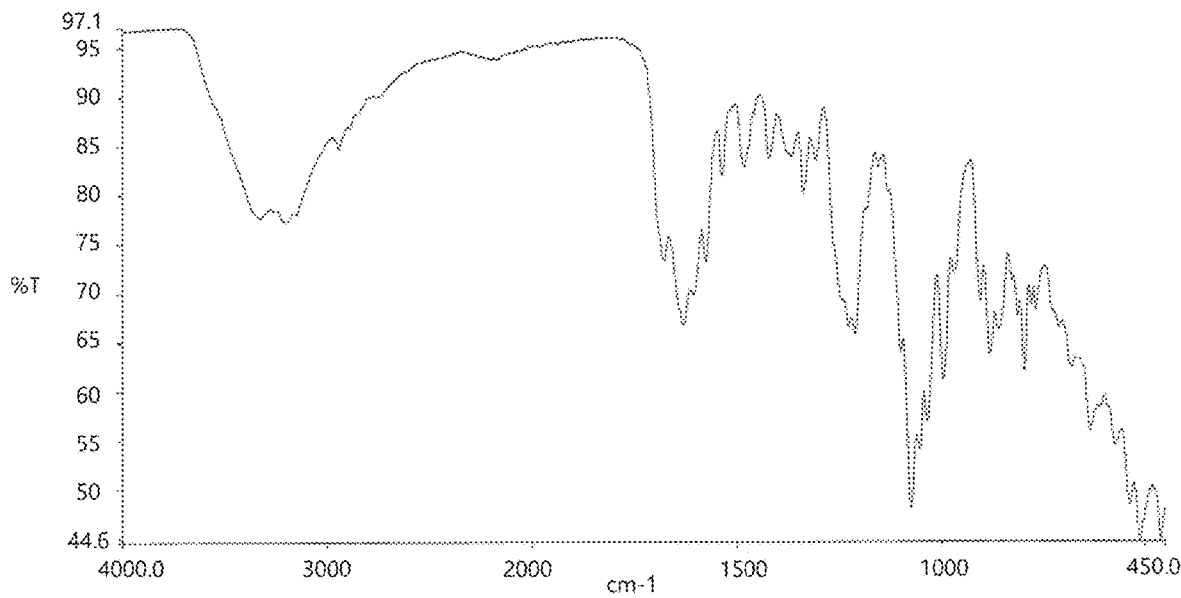

[Fig. 5]
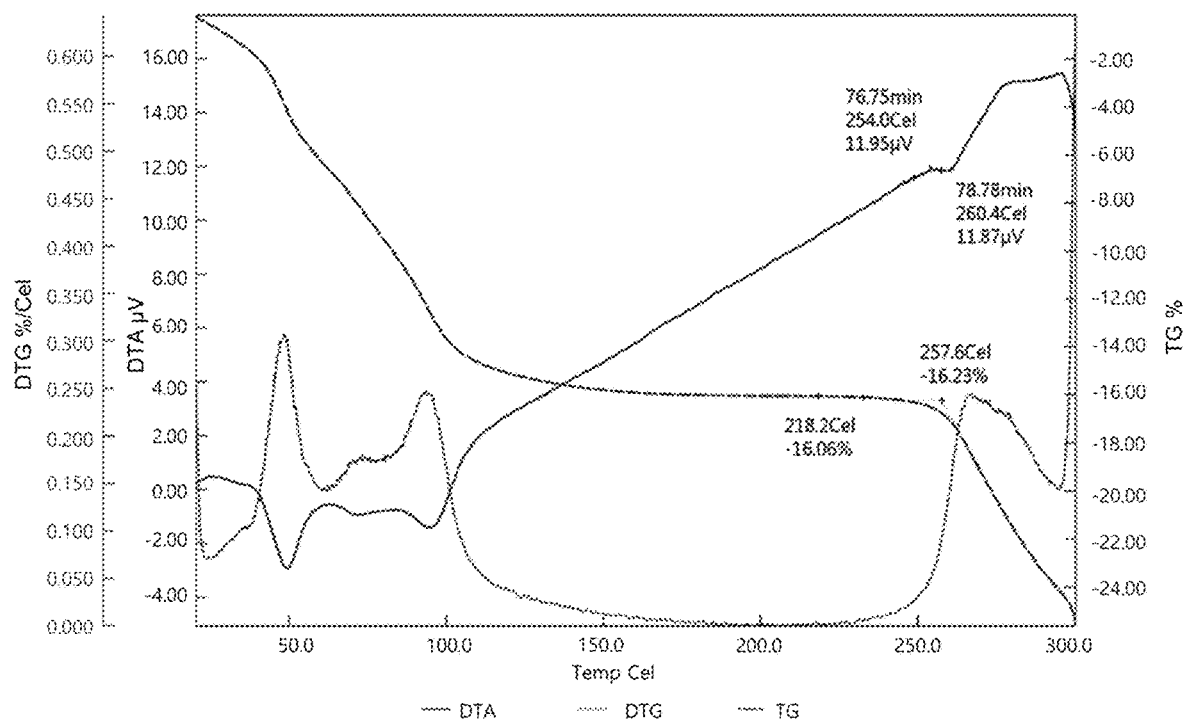
[Fig. 6]
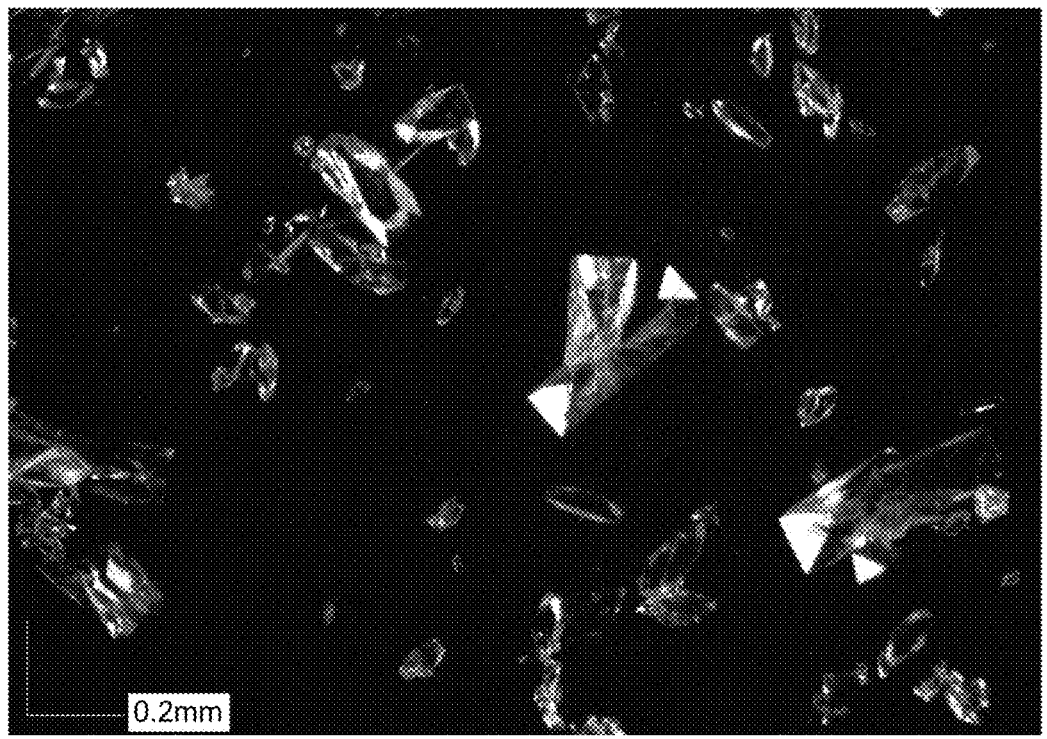

[Fig. 7]
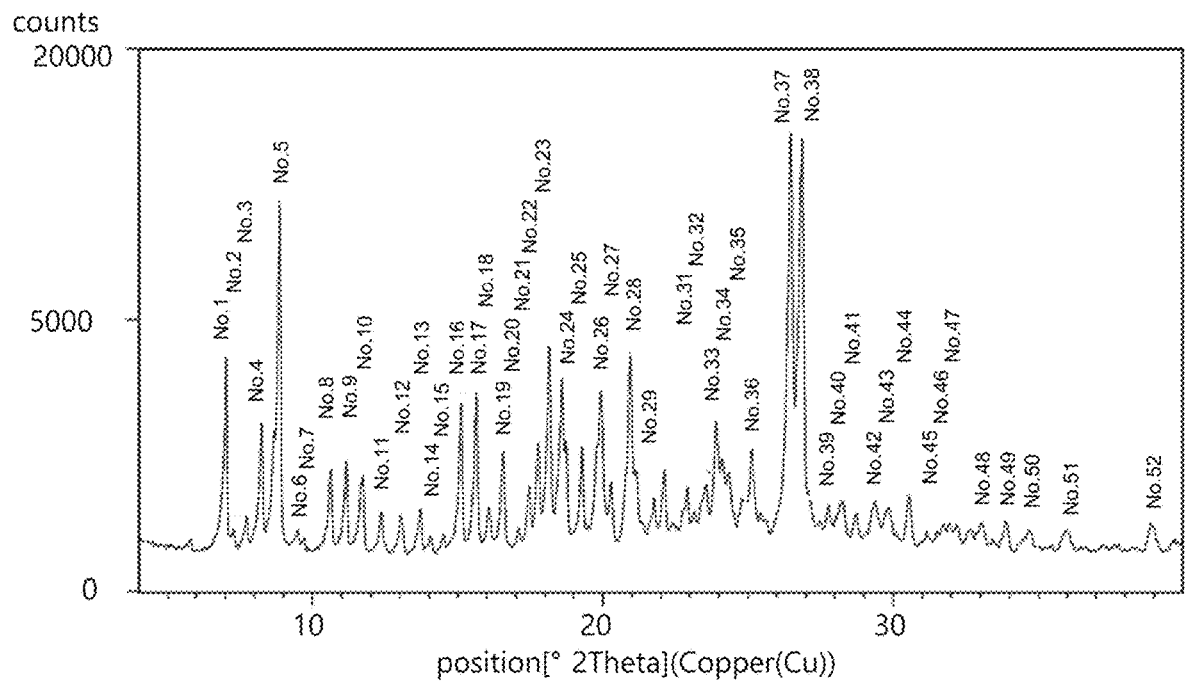
[Fig. 8]
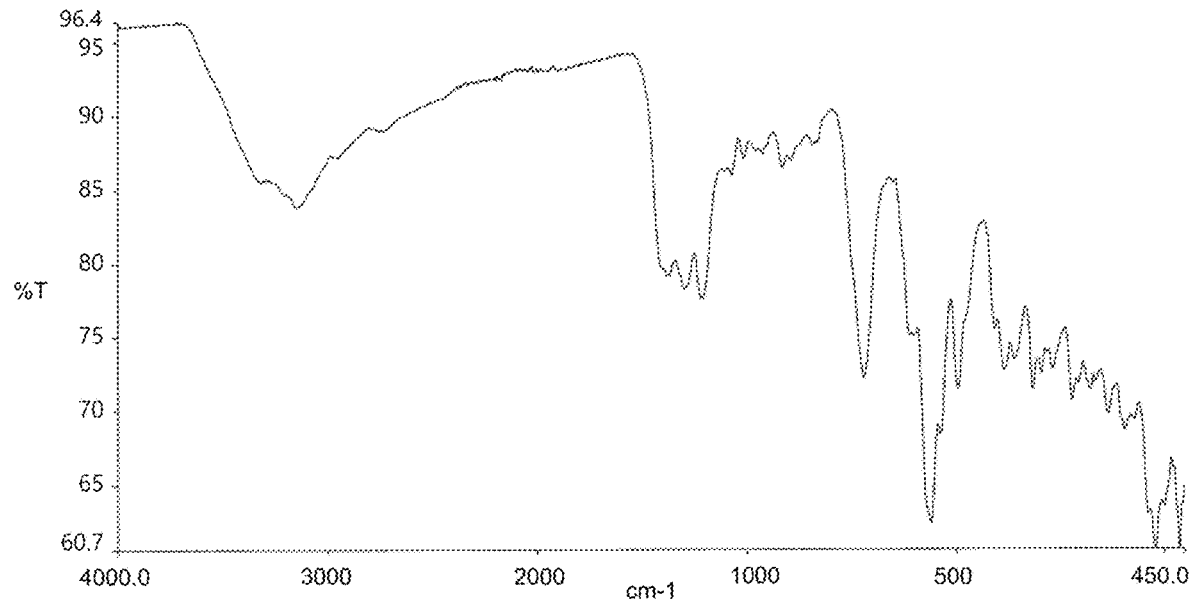

[Fig. 9]
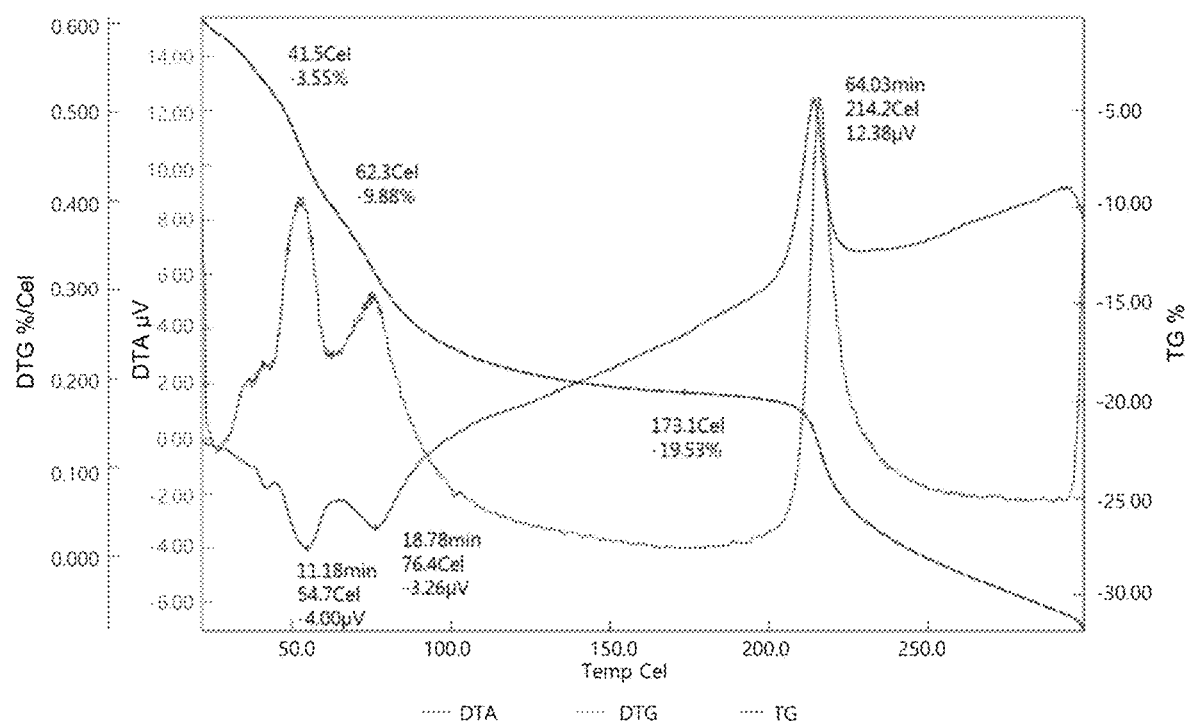
[Fig. 10]
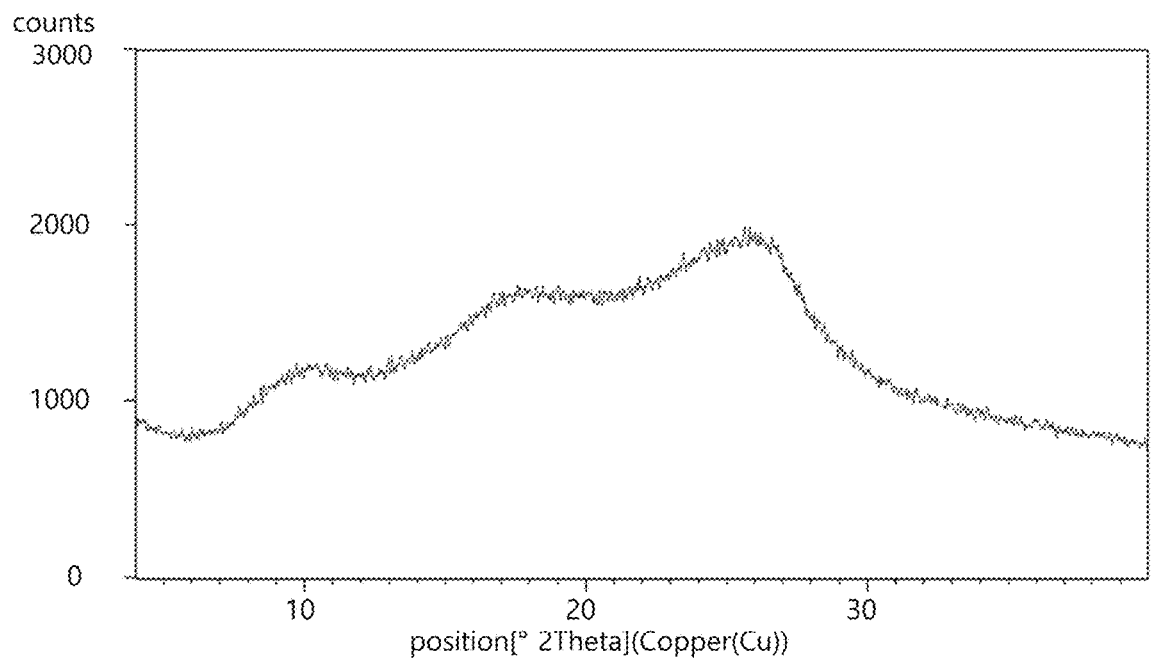

[Fig. 11]
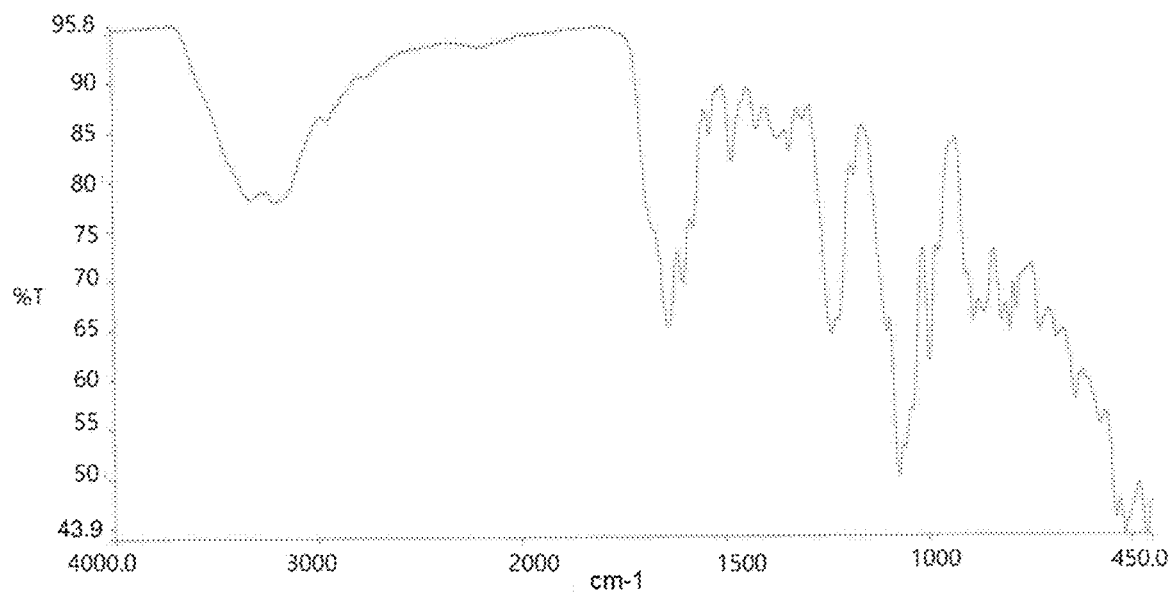
[Fig. 12]
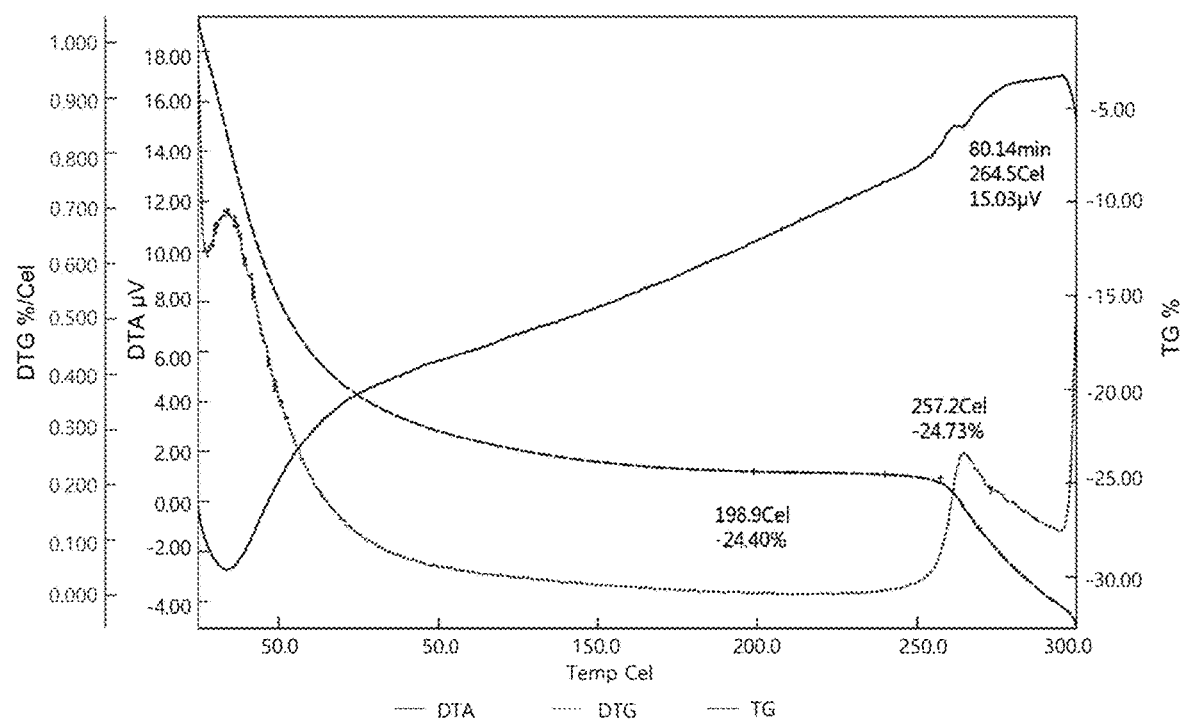

HYDRATE CRYSTAL OF 3',3'-CGAMP

TECHNICAL FIELD

The present invention relates to a hydrate crystal of 3',3'-cyclic GMP-AMP (3',3'-cGAMP), which is considered to be a useful substance as an adjuvant, and a process for producing the crystal.

BACKGROUND ART

Here, 3',3'-cGAMP is a signaling molecule that participates in an increase in production of type I interferon (IFN) in cells, and has recently been expected to be applicable as an adjuvant, antiviral drug, or anti-cancer drug (Patent Literature 1). Examples of an already known process for synthesizing 3',3'-cGAMP include a chemical synthesis process or a synthesis process using a cyclic GMP-AMP synthase derived from, for instance, *Geobacter sulfurreducens* or *Vibrio cholerae* (Non-Patent Literatures 1, 2, and 3).

Currently available 3',3'-cGAMP is either a lyophilized product or an ethanol precipitate. Some commercially available products are marketed as crystalline solids. However, it has been found that after purchase and analysis, any of them is amorphous and, when crushed, can be spread without cracking. FIG. 1 shows, for instance, how it looked at that time. In addition, each product is highly hygroscopic and becomes like glaze in a few minutes. This has revealed that none of the commercially available 3',3'-cGAMP crystalline solids is crystalline.

CITATION LIST

Patent Literature

[Patent Literature 1] Re-publication of PCT International Publication No. 2016-079899

Non Patent Literature

[Non-Patent Literature 1] Ming C. Hammond, et al., PNAS, 2016, 113(7), 1790-1795
[Non-Patent Literature 2] John J. Mekalanos, et al., Cell, 2012, 149, 358-370
[Non-Patent Literature 3] Dinshaw J. Patel, et al., Cell, 2013, 153(5), 1094-1107

SUMMARY OF INVENTION

Technical Problem

Among commonly known 3',3'-cGAMP is a lyophilized product. The lyophilized product needs a lyophilizer during the manufacture. This, itself, causes a limitation in scale-up for mass production. Thus, it has been desired to develop and obtain a large amount of their crystals in a simple manner without using a special apparatus such as a lyophilizer. In addition, conventionally known lyophilized products or ethanol precipitates are highly hygroscopic. Hence, the present invention addresses the problem of providing an easy-to-handle crystal with excellent shelf life.

Solution to Problem

The present inventors have conducted intensive research on crystallization of 3',3'-cGAMP and, as a result, has obtained a hydrate crystal of 3',3'-cGAMP for the first time. In this way, the invention has been completed.

Advantageous Effects of Invention

A hydrate crystal of 3',3'-cGAMP according to the invention may be either a crystal of alkali metal salt or a crystal of free acid. Either is less hygroscopic than existing powder. Thus, each is easy to handle in various purposes and is thus useful as a pharmaceutical raw material or the like. Note that the wording "less hygroscopic" herein refers to the case where after (A) allowed to stand for 1 day under conditions at a temperature of 30° C. and a humidity of 43% and then (B) allowed to stand for 3 days under conditions at a temperature of 30° C. and a humidity of 93%, a substance of interest has a moisture content of 25% or less at the end point (B) and the difference in the moisture content between the end point (A) and the end point (B) is within ±5%.

In addition, among 3',3'-cGAMP hydrate crystals of the invention, a crystal of alkali metal salt may be prepared by a simple process including adjusting a 3',3'-cGAMP aqueous solution at pH 4 to 11 and then adding an organic solvent; and a crystal of free acid may be prepared by a simple process including adding an acid to a 3',3'-cGAMP aqueous solution and then lowering pH to 1 to 3.

BRIEF DESCRIPTION OF DRAWINGS

FIG. 1 is a photograph showing how a commercially available 3',3'-cGAMP crystalline solid looked when spread.

FIG. 2 is a crystal image of crystals of 3',3'-cGAMP sodium salt.

FIG. 3 is an X-ray diffraction spectrum of a crystal of 3',3'-cGAMP sodium salt.

FIG. 4 is an infrared absorption spectrum of a crystal of 3',3'-cGAMP sodium salt.

FIG. 5 shows the results of thermogravimetry/differential thermal analysis of a crystal of 3',3'-cGAMP sodium salt.

FIG. 6 is a crystal image of crystals of 3',3'-cGAMP free acid.

FIG. 7 is an X-ray diffraction spectrum of a crystal of 3',3'-cGAMP free acid.

FIG. 8 is an infrared absorption spectrum of a crystal of 3',3'-cGAMP free acid.

FIG. 9 shows the results of thermogravimetry/differential thermal analysis of a crystal of 3',3'-cGAMP free acid.

FIG. 10 is an X-ray diffraction spectrum of a 3',3'-cGAMP lyophilized product.

FIG. 11 is an infrared absorption spectrum of a 3',3'-cGAMP lyophilized product.

FIG. 12 shows the results of thermogravimetry/differential thermal analysis of a 3',3'-cGAMP lyophilized product.

DESCRIPTION OF EMBODIMENTS

The invention provides a hydrate crystal of 3',3'-cGAMP represented by the following structural formula. Note that unless otherwise indicated, the term "3',3'-cGAMP" herein refers to c[G(3',5')pA(3',5')p] shown below.

[Chemical Formula 1]

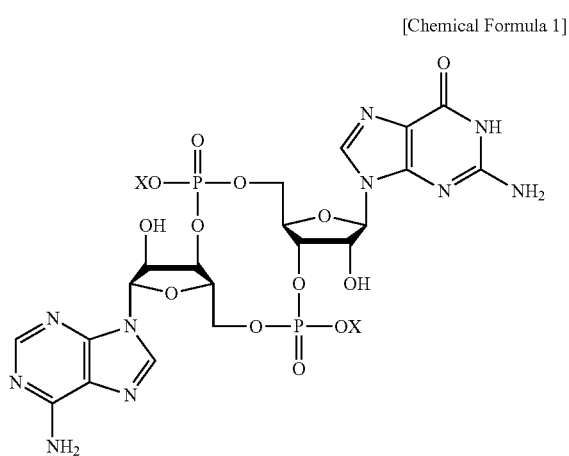

The hydrate crystal of 3',3'-cGAMP according to the invention may be any of a crystal of alkali metal salt or a crystal of free acid. Specifically, X denoted in the above chemical formula 1 may be an alkali metal (Li, Na, K, Rb, Cs, or Fr) or hydrogen (H). In addition, a crystal of sodium salt is particularly preferable among the above crystals of alkali metal salts. Hereinafter, in the case of a crystal of alkali metal salt, the crystal of sodium salt will be described and exemplified as a representative example.

When the moisture content is measured by the Karl-Fischer method, the hydrate crystal of the invention had a moisture content of from 5.0 to 30.0%; and in particular, the moisture content is preferably from 5.0 to 25.0% as demonstrated in Examples below. Specifically, 2.0 to 16.1 water molecules and, in particular, preferably 2.0 to 12.0 water molecules per 3',3'-cGAMP molecule are bonded or attached to the hydrate crystal of 3',3'-cGAMP according to the invention.

The crystal of sodium salt, a preferable crystal, among the crystals of alkali metal salts in the invention is exemplified and illustrated. Here, the crystal of sodium salt can be obtained as a cubic crystal (see FIG. 2).

In addition, the crystal of sodium salt according to the invention is analyzed with a powder X-ray diffractometer using a Cu-Kα beam. Then, there are characteristic peaks of diffraction angle (2θ) at or near 9.3, 10.0, 11.7, 14.4, 17.3, 19.1, 20.3, 22.6, 23.3, 23.8, 24.3, 25.6, and 28.2 (°) as demonstrated in Examples below (see FIG. 3).

Note that generally speaking, the diffraction angles (2θ) in powder X-ray diffraction may include less than 5% error. Examples of the crystal of sodium salt according to the invention include crystals with perfectly matched diffraction angle peaks in the powder X-ray diffraction as well as crystals with the diffraction angle peaks matched within less than 5% error. For instance, in the powder X-ray diffraction, there are characteristic peaks of diffraction angle (2θ) at 9.3±0.5, 10.0±0.5, 11.7±0.6, 14.4±0.7, 17.3±0.9, 19.1±1.0, 20.3±1.0, 22.6±1.1, 23.3±1.2, 23.8±1.2, 24.3±1.2, 25.6±1.3, and 28.2±1.4 (°).

When an infrared absorption spectrum of the crystal of sodium salt according to the invention is measured, there are characteristic peaks at or near 3328, 3200, 1677, 1629, 1604, 1225, 1209, 1073, and 1052 (cm$^{-1}$) (see FIG. 4).

Note that when an infrared absorption spectrum is measured, in general, less than 2 (cm$^{-1}$) error may be included. Examples of the crystal of sodium salt according to the invention include crystals with peak positions perfectly matched to the above numbers in the infrared absorption spectrum as well as crystals with the peaks matched within less than 2 cm$^{-1}$ error. When an infrared absorption spectrum thereof is measured, for instance, there are characteristic peaks at 3328±1.9, 3200±1.9, 1677±1.9, 1629±1.9, 1604±1.9, 1225±1.9, 1209±1.9, 1073±1.9, and 1052±1.9 (cm$^{-1}$).

When the crystal of sodium salt according to the invention is analyzed with a thermogravimetry/differential thermal analysis (TG/DTA) device (at a programming rate of 5° C./min), there is no endothermic peak (see FIG. 5).

When measured by atomic absorption spectrophotometry, the crystal of sodium salt according to the invention has a sodium content of from 3 to 9.5% (w/w). Specifically, the crystal of sodium salt according to the invention may contain 1 to 3 sodium molecules. Meanwhile, the crystal containing 5 to 7% (w/w), namely 2 sodium molecules, in particular, is preferable because the pH thereof when dissolved is neutral and use thereof is thus high.

By contrast, a crystal of free acid according to the invention can be obtained as an octahedral crystal (see FIG. 6).

Here, the crystal of free acid according to the invention is analyzed with a powder X-ray diffractometer using a Cu-Kα beam. Then, there are characteristic peaks of diffraction angle (2θ) at or near 7.0, 8.3, 8.9, 15.1, 15.7, 18.2, 18.6, 20.0, 20.9, 26.5, and 26.9 (°) as demonstrated in Examples below (see FIG. 7).

Note that generally speaking, the diffraction angles (2θ) in powder X-ray diffraction may include less than 5% error. Examples of the crystal of free acid according to the invention include crystals with perfectly matched diffraction angle peaks in the powder X-ray diffraction as well as crystals with the diffraction angle peaks matched within less than 5% error. For instance, in the powder X-ray diffraction, there are characteristic peaks of diffraction angle (2θ) at 7.0±0.4, 8.3±0.4, 8.9±0.4, 15.1±0.8, 15.7±0.8, 18.2±0.9, 18.6±0.9, 20±1.0, 20.9±1.0, 26.5±1.3, and 26.9±1.3 (°).

When an infrared absorption spectrum of the crystal of free acid according to the invention is measured, there are characteristic peaks at or near 3146, 1688, 1645, 1605, 1218, and 1059 (cm$^{-1}$) (see FIG. 8).

Note that when an infrared absorption spectrum is measured, in general, less than 2 (cm$^{-1}$) error may be included. Examples of the crystal of free acid according to the invention include crystals with peak positions perfectly matched to the above numbers in the infrared absorption spectrum as well as crystals with the peaks matched within less than 2 cm$^{-1}$ error. When an infrared absorption spectrum thereof is measured, for instance, there are characteristic peaks at 3146±1.9, 1688±1.9, 1645±1.9, 1605±1.9, 1218±1.9, and 1059±1.9 (cm$^{-1}$).

When the crystal of free acid according to the invention is analyzed with a thermogravimetry/differential thermal analysis (TG/DTA) device (at a programming rate of 5° C./min), there is an endothermic peak at or near 260° C. (see FIG. 9).

When the purity of a hydrate crystal of 3',3'-cGAMP according to the invention is determined by high performance liquid chromatography, the purity is 97% or higher and preferably 99% or higher.

Next, how to prepare a hydrate crystal of 3',3'-cGAMP according to the invention will be described. Here, 3',3'-cGAMP to be crystallized may be synthesized by a known procedure such as an enzymatic synthesis process or a chemical synthesis process. The enzymatic synthesis should follow an existing protocol. For instance, the protocol described in Non-Patent Literature 1 or 2 may be used. After the reaction, 3',3'-cGAMP produced in the reaction solution may be purified using active carbon or reverse-phase chromatography.

How to obtain a crystal of alkali metal salt according to the invention will be described and exemplified using a crystal of sodium salt. The crystal of sodium salt may be obtained by adjusting a 3',3'-cGAMP aqueous solution at pH 4 to 11 and adding an organic solvent.

To crystallize and obtain the sodium salt in a higher yield, the following steps are preferably carried out, including: (1) preparing a 3',3'-cGAMP aqueous solution to have an optical density $OD_{260}$ at from 500 to 20,000 when measured at a wavelength of 260 nm; (2) heating the 3',3'-cGAMP aqueous solution to 50 to 70° C.; (3) adding an acid or base to the 3',3'-cGAMP aqueous solution to adjust a pH to 4 to 11; (4) adding an organic solvent to the 3',3'-cGAMP aqueous solution; (5) cooling the 3',3'-cGAMP aqueous solution to 1 to 20° C.

Examples of the acid used in step (3) include, but are not limited to, hydrochloric acid, sulfuric acid, or nitric acid. Examples of the base used include, but are not limited to, sodium hydroxide. It is preferable to gently add the acid or base so as to prevent amorphous from being precipitated or to prevent crystals from being rapidly precipitated after the rapid addition.

Examples of the organic solvent used in step (4) include, but are not limited to, alcohols containing 6 or less carbon atoms such as methanol and ethanol, ketones such as acetone, ethers such as dioxane, nitriles such as acetonitrile, or amides such as dimethylformamide.

Further, steps (2) and (3) may be carried out at the same time. Likewise, steps (4) and (5) may be carried out at the same time.

During free acid crystallization, a crystal of free acid may be obtained by adding an acid to a 3',3'-cGAMP aqueous solution; and lowering a pH to 1 to 3 and preferably 1.5 to 2.0.

To crystallize and obtain the free acid in a higher yield, the following steps are preferably carried out, including: (1) preparing a 3',3'-cGAMP aqueous solution to have an optical density $OD_{260}$ at from 10 to 15,000 when measured at a wavelength of 260 nm; (2) heating the 3',3'-cGAMP aqueous solution to 50 to 70° C.; (3) adding an acid to the 3',3'-cGAMP aqueous solution to lower a pH to 1 to 3; (4) cooling the 3',3'-cGAMP aqueous solution to 1 to 20° C.

Examples of the acid used in step (3) include, but are not limited to, hydrochloric acid, sulfuric acid, or nitric acid. It is preferable to gently add the acid so as to prevent crystals from becoming amorphous or being rapidly precipitated after the rapid addition.

Further, steps (2) and (3) may be carried out at the same time. Alternatively, steps (3) and (4) may be carried out at the same time.

The 3',3'-cGAMP crystals produced by the above production processes may be each filtered and then dried to yield a product. For the drying, it is possible to use, if appropriate, a procedure such as vacuum drying.

EXAMPLES

Hereinafter, the invention will be specifically described by referring to Examples. It is clear that the invention, however, is not limited to them.

(Example 1) to Produce Crystal of 3',3'-cGAMP Sodium Salt

First, 3',3'-cGAMP was enzymatically synthesized and then purified in accordance with a known procedure. The resulting purified 3',3'-cGAMP solution (10 mL) at pH 8.5 and with an OD260 of 6200 was heated to 30° C. in an incubator. Next, 12 mL of ethanol was gently added thereto while stirring. To the mixture were added 20 mg of seed crystals, which had been obtained by layering ethanol on the 3',3'-cGAMP solution adjusted at pH 8.5. Then, whether the seed crystals were not dissolved was checked.

After the addition of seed crystals, the solution was cooled to a temperature of 5° C. to precipitate crystals. The resulting crystals so precipitated were filtered through a membrane filter (3 µm) to yield wet crystals. The wet crystals were dried at 30° C. for 1 h to give 0.96 g of dry crystals.

The results of instrumental analysis of the crystal of 3',3'-cGAMP sodium salt as prepared in the above Example 1 are shown.

(Instrumental Analysis)

(A) Purity Test

The purity of the crystalline 3',3'-cGAMP sodium salt obtained in Example 1 was analyzed by high performance liquid chromatography. As a result, the purity of 3',3'-cGAMP was 99.7%. Note that the high performance liquid chromatography was performed under the following conditions.

(Conditions)

Column: Hydrosphere C18 (manufactured by YMC, Inc.)
Eluent: 0.1 mol/L TEA-P (pH 6.0)+5% acetonitrile
Detection method: detection at UV260 nm Meanwhile, the crystals were stored at 60° C. and subjected to a stability test. Then, the 3',3'-cGAMP was not apparently decomposed, and was thus very stable under high temperature conditions.

(B) Crystal Form

FIG. 2 is a representative photograph showing the crystals of 3',3'-cGAMP sodium salt as prepared in Example 1. FIG. 2 shows that the crystal of 3',3'-cGAMP sodium salt according to the invention was found to have a cubic crystal form.

(C) Moisture Content

In Example 1, the crystals of 3',3'-cGAMP sodium salt were prepared. Here, the crystal moisture content immediately after drying was measured by the Karl-Fischer method. As a result, the moisture content was 7.9%. Specifically, it was revealed that in the crystal of 3',3'-cGAMP sodium salt immediately after drying in the invention, 3 to 4 water molecules were bonded or attached to one 3',3'-cGAMP molecule. In addition, the crystals were stored at a humidity of 43% for 1 day so as to stabilize their moisture content. The moisture content was likewise measured. As a result, the moisture content was 18.1%. That is, it was revealed that in the crystal of 3',3'-cGAMP sodium salt stored at a humidity of 43% for 1 day in the invention, 7 to 8 water molecules were bonded or attached to one 3',3'-cGAMP molecule.

(D) Powder X-Ray Diffraction

A crystal of 3',3'-cGAMP sodium salt according to the invention was subjected to X-ray diffraction spectrometry using an X-ray diffractometer X'Pert PRO MPD (Spectris) under the following measurement conditions.

(Measurement Conditions)

Target: Cu
X-ray tube current: 40 mA
X-ray tube voltage: 45 kV
Scanning range: 2θ=4.0 to 40.0°
Pretreatment: pulverization using an agate mortar FIG. 3 and Table 1 show that the crystal of 3',3'-cGAMP sodium salt according to the invention had characteristic peaks of diffraction angle (2θ) at or near 9.3, 10.0, 11.7, 14.4, 17.3, 19.1, 20.3, 22.6, 23.3, 23.8, 24.3, 25.6, and 28.2 (°).

TABLE 1

| Pos.<br>[° 2Th.] | d-spacing<br>[Å] | NET<br>Intensity<br>(cts) | Relative<br>intensity (%) |
|---|---|---|---|
| 9.3 | 9.50 | 4515 | 28.85 |
| 10.0 | 8.87 | 4443 | 28.39 |
| 11.7 | 7.56 | 2692 | 17.2 |
| 11.9 | 7.41 | 1115 | 7.12 |
| 14.4 | 6.14 | 7073 | 45.2 |
| 16.7 | 5.32 | 1146 | 7.33 |
| 17.3 | 5.13 | 1584 | 10.12 |
| 19.1 | 4.65 | 15649 | 100 |
| 20.3 | 4.37 | 2080 | 13.29 |
| 21.0 | 4.33 | 1035 | 6.61 |
| 21.3 | 4.17 | 954 | 6.1 |
| 22.6 | 3.94 | 1569 | 10.02 |
| 23.3 | 3.82 | 2673 | 17.08 |
| 23.8 | 3.74 | 2346 | 14.99 |
| 24.3 | 3.67 | 2691 | 17.2 |
| 25.6 | 3.49 | 8394 | 53.64 |
| 27.0 | 3.30 | 933 | 5.96 |
| 27.5 | 3.24 | 1332 | 8.51 |
| 28.2 | 3.16 | 1803 | 11.52 |

(E) Infrared Absorption Spectrum

A crystal of 3',3'-cGAMP sodium salt according to the invention was subjected to infrared absorption spectroscopy using a Fourier transform infrared spectrophotometer Spectrum One (Perkin Elmer) and the Attenuated Total Reflectance (ATR) method.

The crystal of 3',3'-cGAMP sodium salt according to the invention had characteristic peaks at or near 3328, 3200, 1677, 1629, 1604, 1225, 1209, 1073, and 1052 (cm$^{-1}$). FIG. 4 shows the results.

(F) Differential Scanning calorimetry

When a crystal of 3',3'-cGAMP sodium salt according to the invention was analyzed with a thermogravimetry/differential thermal analysis (TG/DTA) device (at a programming rate of 5° C./min), there was no endothermic peak (see FIG. 5).

(G) Sodium Content

The sodium content of the crystal of 3',3'-cGAMP sodium salt as prepared in Example 1 was measured by atomic absorption spectrophotometry. The results have revealed that the sodium content was 6.2% (w/w), indicating inclusion of 2 sodium molecules.

(Example 2) to Produce Crystal of 3',3'-cGAMP Free Acid

First, 3',3'-cGAMP was enzymatically synthesized and then purified in accordance with a known procedure. The resulting purified 3',3'-cGAMP solution (360 mL) with an OD$_{260}$ of 168 was heated to 60° C. in an incubator. Next, 1 mol/L hydrochloric acid solution was gently added thereto while stirring such that the pH was adjusted to 1.5.

After the addition of hydrochloric acid solution, the solution was cooled to a temperature of 5° C. to precipitate crystals. The resulting crystals so precipitated were filtered through a glass filter (17G3) to yield wet crystals. The wet crystals were dried at 30° C. for 1 h to give 1.63 g of dry crystals.

The results of instrumental analysis of the crystal of 3',3'-cGAMP free acid as prepared in the above Example 2 are shown.

(Instrumental Analysis)

(A) Purity Test

The purity of the crystalline 3',3'-cGAMP obtained in this Example was analyzed by high performance liquid chromatography. As a result, the purity of 3',3'-cGAMP was 99.5%. Note that the high performance liquid chromatography was performed under the following conditions.

(Conditions)
Column: Hydrosphere C18 (manufactured by YMC, Inc.)
Eluent: 0.1 mol/L TEA-P (pH 6.0)+5% acetonitrile
Detection method: detection at UV260 nm Meanwhile, the crystals were stored at 60° C. and subjected to a stability test. Then, the 3',3'-cGAMP was not apparently decomposed, and was thus very stable under high temperature conditions.

(B) Crystal Form

FIG. 6 is a representative photograph showing the crystals of 3',3'-cGAMP free acid as prepared in Example 2. FIG. 6 shows that the crystal of 3',3'-cGAMP free acid according to the invention was found to have a octahedral crystal form.

(C) Moisture Content Measurement

The crystals of 3',3'-cGAMP free acid as prepared in Example 2 were stored at a humidity of 43% for 1 day so as to stabilize their moisture content. Then, the crystal moisture content was measured by the Karl-Fischer method. As a result, the moisture content was 24.7%. Specifically, it was revealed that in the crystal of 3',3'-cGAMP free acid according to the invention, 12 to 13 water molecules were bonded to or attached to one 3',3'-cGAMP molecule.

(D) Powder X-Ray Diffraction

A crystal of 3',3'-cGAMP free acid according to the invention was subjected to X-ray diffraction spectrometry using an X-ray diffractometer X'Pert PRO MPD (Spectris) under the following measurement conditions.

(Measurement Conditions)
Target: Cu
X-ray tube current: 40 mA
X-ray tube voltage: 45 kV
Scanning range: 2θ=4.0 to 40.0°
Pretreatment: pulverization using an agate mortar FIG. 7 and Table 2 show that the crystal of 3',3'-cGAMP free acid according to the invention had characteristic peaks of diffraction angle (2θ) at or near 7.0, 8.3, 8.9, 15.1, 15.7, 18.2, 18.6, 20.0, 20.9, 26.5, and 26.9 (°).

TABLE 2

| Pos.<br>[° 2Th.] | d-spacing<br>[Å] | NET<br>Intensity<br>(cts) | Relative<br>intensity (%) |
|---|---|---|---|
| 7.0 | 12.6 | 3491 | 47.19 |
| 8.3 | 10.7 | 2335 | 31.56 |
| 8.9 | 9.97 | 6295 | 85.09 |
| 10.6 | 8.32 | 1463 | 19.77 |
| 11.2 | 7.93 | 1674 | 22.63 |
| 11.7 | 7.56 | 1803 | 17.61 |
| 12.4 | 7.16 | 775 | 10.47 |
| 13.7 | 6.45 | 770 | 10.41 |
| 15.1 | 5.86 | 2651 | 35.84 |
| 15.7 | 5.66 | 2804 | 37.9 |
| 16.1 | 5.51 | 7474 | 10.1 |
| 16.6 | 5.35 | 1746 | 23.6 |
| 17.4 | 5.08 | 1018 | 13.77 |
| 17.8 | 4.99 | 1828 | 24.71 |
| 18.2 | 4.88 | 3555 | 48.05 |
| 18.6 | 4.77 | 2985 | 40.85 |
| 19.3 | 4.60 | 1688 | 22.82 |
| 20.0 | 4.45 | 2608 | 35.25 |
| 20.3 | 4.38 | 1008 | 13.63 |
| 20.9 | 4.24 | 3311 | 44.76 |
| 22.1 | 4.02 | 1149 | 15.53 |
| 22.9 | 3.89 | 747 | 10.09 |
| 23.6 | 3.78 | 875 | 11.83 |
| 23.9 | 3.73 | 2055 | 27.77 |
| 24.1 | 3.70 | 1365 | 18.45 |

TABLE 2-continued

| Pos. [° 2Th.] | d-spacing [Å] | NET Intensity (cts) | Relative intensity (%) |
|---|---|---|---|
| 24.3 | 3.66 | 1110 | 15.01 |
| 25.1 | 3.55 | 1526 | 20.68 |
| 26.5 | 3.36 | 7398 | 100 |
| 26.9 | 3.32 | 7287 | 98.5 |
| 30.5 | 2.93 | 846 | 11.44 |

(E) Infrared Absorption Spectrum

A crystal of 3',3'-cGAMP free acid according to the invention was subjected to infrared absorption spectroscopy using a Fourier transform infrared spectrophotometer Spectrum One (Perkin Elmer) and the Attenuated Total Reflectance (ATR) method.

The crystal of 3',3'-cGAMP free acid according to the invention had characteristic peaks at or near 3146, 1688, 1645, 1605, 1218, and 1059 (cm$^{-1}$). FIG. 8 shows the results.

(F) Differential Scanning calorimetry

When a crystal of 3',3'-cGAMP free acid according to the invention was analyzed with a thermogravimetry/differential thermal analysis (TG/DTA) device (at a programming rate of 5° C./min), there was an endothermic peak at or near about 260° C. (see FIG. 9).

(Reference Example) to Produce Lyophilized Product of 3',3'-cGAMP

First, 500 mg of crystals of 3',3'-cGAMP free acid were suspended in 10 mL of water. Next, 1 mol/L NaOH solution was added to adjust the pH to 8.5. In this way, the suspended 3',3'-cGAMP crystals were dissolved.

The dissolved 3',3'-cGAMP solution was appropriately diluted and then lyophilized to yield a lyophilized product of 3',3'-cGAMP sodium salt.

The results of instrumental analysis of the 3',3'-cGAMP lyophilized product prepared in the above Reference Example are shown.

(Instrumental Analysis)

(A) Purity Test

The purity of 3',3'-cGAMP in the lyophilized product obtained in this Reference Example was analyzed by high performance liquid chromatography. As a result, the purity of 3',3'-cGAMP was 99.7%. Note that the high performance liquid chromatography was performed under the following conditions.

(Conditions)
Column: Hydrosphere C18 (manufactured by YMC, Inc.)
Eluent: 0.1 M TEA-P (pH 6.0)+5% acetonitrile
Detection method: detection at UV260 nm (B) Powder X-Ray Diffraction The 3',3'-cGAMP sodium salt lyophilized product in the invention was subjected to X-ray diffraction spectrometry using an X-ray diffractometer X'Pert PRO MPD (Spectris) under the following measurement conditions.

(Measurement Conditions)
Target: Cu
X-ray tube current: 40 mA
X-ray tube voltage: 45 kV
Scanning range: 2θ=4.0 to 40.0°
Pretreatment: pulverization using an agate mortar FIG. 10 shows that the 3',3'-cGAMP lyophilized product exhibited no peaks.

(C) Infrared Absorption Spectrum

The 3',3'-cGAMP sodium salt lyophilized product in the invention was subjected to infrared absorption spectroscopy using a Fourier transform infrared spectrophotometer Spectrum One (Perkin Elmer) and the Attenuated Total Reflectance (ATR) method.

The 3',3'-cGAMP lyophilized product had characteristic peaks at or near 3319, 3194, 1637, 1600, 1235, 1218, 1072, and 1055 (cm$^{-1}$). FIG. 11 shows the results.

(D) Differential Scanning calorimetry

When the 3',3'-cGAMP lyophilized product in the invention was analyzed with a thermogravimetry/differential thermal analysis (TG/DTA) device (at a programming rate of 5° C./min), there was no endothermic peak (see FIG. 12).

Example 3

The crystals obtained in the above Examples 1 and 2 as well as the lyophilized product obtained in the Reference Example were allowed to stand for 3 days in a desiccator filled with a saturated potassium nitrate solution and kept at a temperature of 30° C. and a humidity of 93%. The moisture content was compared between before and after the standing by the Karl-Fischer method. Table 3 shows the results.

TABLE 3

|  | Before standing | After standing | Δ Moisture content |  |
|---|---|---|---|---|
| Reference Example | 12.94 | 36.01 | +23.07 |  |
| Example 1 | 18.10 | 21.60 | +3.50 |  |
| Example 2 | 24.71 | 23.09 | −1.62 | (%) |

As demonstrated in Table 3, the 3',3'-cGAMP crystals that belong to the invention have better humidity resistance than the existing lyophilized product.

The invention claimed is:

1. A hydrate crystal of 3',3'-cyclic GMP-AMP represented by the following structure:

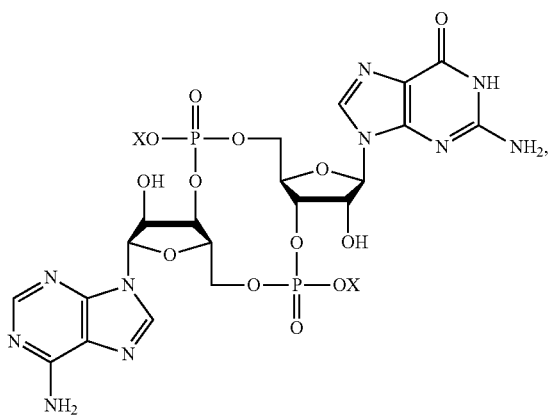

wherein X is an alkali metal or hydrogen, and the hydrate crystal has a moisture content of 5.0 to 30.0% as measured by the Karl-Fischer method.

2. The hydrate crystal of claim 1, wherein X is an alkali metal.

3. A process for producing the hydrate crystal of claim 1, comprising the steps of:
 adding an acid or a base to adjust a 3',3'-cyclic GMP-AMP aqueous solution at to pH 4 to 11; and
 adding an organic solvent to precipitate and obtain a crystal,
 wherein X is an alkali metal, and the organic solvent comprises an alcohol containing 6 or fewer carbons, a ketone, an ether, a nitrile, or an amide.

4. The hydrate crystal of claim 1, wherein X is hydrogen.

5. A process for producing the hydrate crystal of claim 4, comprising
 adding an acid to a 3',3'-cyclic GMP-AMP aqueous solution to adjust its pH to 3 to 1 to precipitate and obtain a crystal.

6. The hydrate crystal of claim 2, wherein X is Na, and the hydrate crystal is characterized by a powder X-ray diffraction pattern comprising characteristic peaks of diffraction angle (2θ) at 9.3±0.5, 10.0±0.5, 11.7±0.6, 14.4±0.7, 17.3±0.9, 19.1±1.0, 20.3±1.0, 22.6±1.1, 23.3±1.2, 23.8±1.2, 24.3±1.2, 25.6±1.3, and 28.2±1.4)(°).

7. The hydrate crystal of claim 2, wherein X is Na, and the hydrate crystal is characterized by an infrared absorption spectrum comprising characteristic peaks at 3328±1.9, 3200±1.9, 1677±1.9, 1629±1.9, 1604±1.9, 1225±1.9, 1209±1.9, 1073±1.9, and 1052±1.9 ($cm^{-1}$).

8. The hydrate crystal of claim 4, wherein the hydrate crystal is characterized by a powder X-ray diffraction pattern comprising characteristic peaks of diffraction angle (2θ) at 7.0±0.4, 8.3±0.4, 8.9±0.4, 15.1±0.8, 15.7±0.8, 18.2±0.9, 18.6±0.9, 20±1.0, 20.9±1.0, 26.5±1.3, and 26.9 1.3)(°).

9. The hydrate crystal of claim 4, wherein the hydrate crystal is characterized by an infrared absorption spectrum comprising characteristic peaks at 3146±1.9, 1688±1.9, 1645±1.9, 1605±1.9, 1218±1.9, and 1059±1.9 ($cm^{-1}$).

* * * * *